(12) United States Patent
Kumar

(10) Patent No.: US 11,857,055 B2
(45) Date of Patent: Jan. 2, 2024

(54) FLUID DISCHARGER AND APPLICATOR DEVICE WITH PRESSING PART

(71) Applicant: Selva Kumar, Houston, TX (US)

(72) Inventor: Selva Kumar, Houston, TX (US)

(\*) Notice: Subject to any disclaimer, the term of this patent is extended or adjusted under 35 U.S.C. 154(b) by 0 days.

(21) Appl. No.: 17/062,588

(22) Filed: Oct. 4, 2020

(65) Prior Publication Data
US 2023/0346102 A1 Nov. 2, 2023

(51) Int. Cl.
| | |
|---|---|
| A45D 34/04 | (2006.01) |
| A45D 40/26 | (2006.01) |
| A61M 35/00 | (2006.01) |
| A61F 13/15 | (2006.01) |
| A45D 34/00 | (2006.01) |

(52) U.S. Cl.
CPC ......... *A45D 34/041* (2013.01); *A45D 40/261* (2013.01); *A61F 13/15* (2013.01); *A61M 35/003* (2013.01); *A45D 2034/005* (2013.01); *A45D 2200/109* (2013.01); *A45D 2200/1018* (2013.01); *A45D 2200/1081* (2013.01)

(58) Field of Classification Search
CPC ............... A45D 34/041; A45D 40/261; A45D 2200/1009; A45D 2200/109; A45D 27/04; A45D 2200/1018; A45D 2200/1081; A61F 13/15; A61M 35/003
USPC ..... 401/23, 184, 186, 188 R, 205, 266, 264, 401/272, 275, 185
See application file for complete search history.

(56) References Cited

U.S. PATENT DOCUMENTS

| | | | | |
|---|---|---|---|---|
| 6,045,279 A | * | 4/2000 | Follis | A45D 34/04 401/6 |
| 6,053,650 A | * | 4/2000 | Bennett | B05C 17/0325 401/208 |
| 6,171,004 B1 | * | 1/2001 | Derhammer | A47L 13/22 401/184 |
| 6,543,950 B1 | * | 4/2003 | Huang | A45D 34/042 401/183 |
| 6,945,722 B2 | * | 9/2005 | Colburn | A46B 11/06 401/11 |
| 6,983,866 B2 | * | 1/2006 | Smart | A45D 34/042 15/104.94 |
| 7,004,659 B1 | * | 2/2006 | Goodman | B05C 17/002 401/265 |
| 7,101,105 B2 | * | 9/2006 | Reggiani | A45D 40/00 401/277 |

(Continued)

*Primary Examiner* — Jennifer C Chiang
(74) *Attorney, Agent, or Firm* — Brett A. Schenck

(57) ABSTRACT

A fluid discharger and applicator device for uniform distribution or application of the fluid for treating the skin or any surface is disclosed. The fluid discharger and applicator device comprises a handle, a dispenser connector and a dispenser member. The handle of the fluid discharger and applicator device is defined with a cavity to store a fluid. The handle is further defined with a dispenser end configured to dispense the fluid stored within the cavity of the handle. The dispenser connector of the fluid discharger and applicator device is removably fastened to the dispenser end of the handle. The dispenser connector is configured to transfer the fluid extruded from the cavity of the handle on the dispenser member, which is operably attached to the dispenser connector. The dispenser member of the fluid discharger and applicator device is configured to apply the fluid on skin of a user.

20 Claims, 28 Drawing Sheets

(56) References Cited

U.S. PATENT DOCUMENTS

| | | | |
|---|---|---|---|
| 7,717,635 B1* | 5/2010 | Schmidig | A46B 11/0055 |
| | | | 401/6 |
| 7,814,917 B2* | 10/2010 | Hurwitz | A46B 11/0062 |
| | | | 132/116 |
| 7,980,777 B2* | 7/2011 | Kennedy | B05C 17/002 |
| | | | 401/188 R |
| 7,984,832 B2* | 7/2011 | Pivonka | A45D 34/04 |
| | | | 222/321.9 |
| 8,267,610 B2* | 9/2012 | Goodman | B05C 17/002 |
| | | | 401/266 |
| 2004/0265042 A1* | 12/2004 | Chan | A47L 17/04 |
| | | | 401/270 |
| 2009/0263176 A1* | 10/2009 | Mileti | A46B 11/0065 |
| | | | 401/184 |
| 2018/0126136 A1* | 5/2018 | Brown | B65D 1/32 |
| 2020/0000202 A1* | 1/2020 | Bruder | B43K 1/006 |

\* cited by examiner

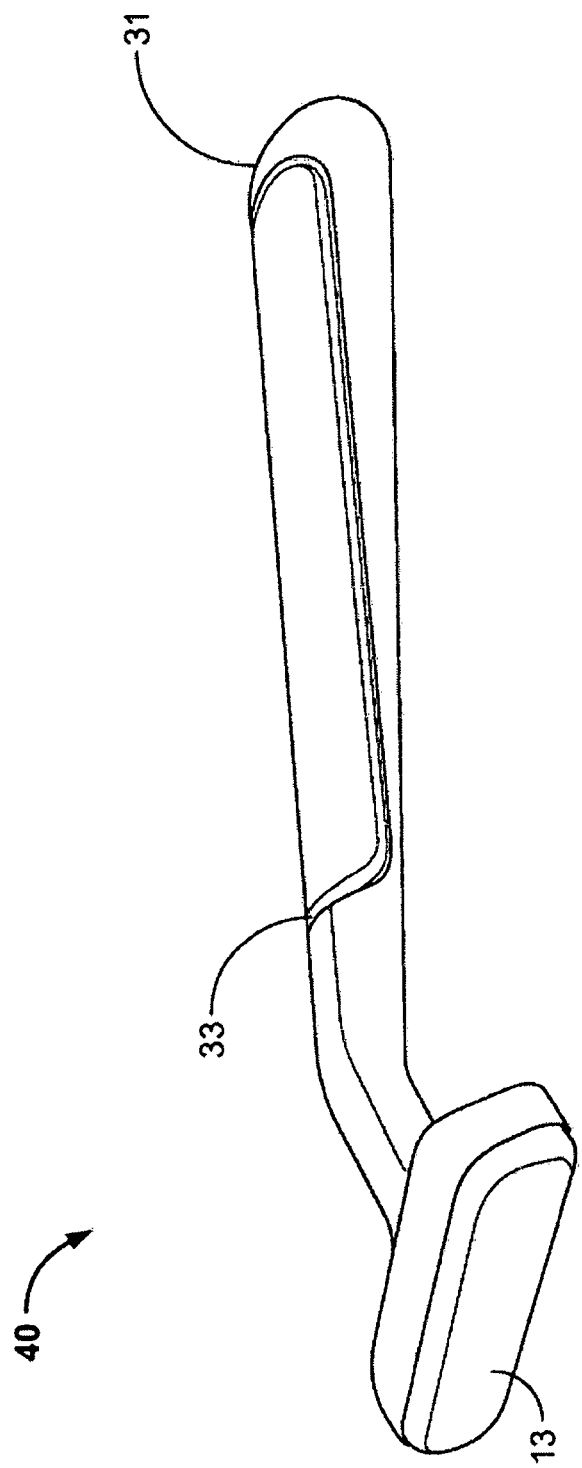

FLUID DISCHARGER AND APPLICATOR DEVICE WITH PRESSING PART

BACKGROUND OF THE INVENTION

A. Technical Field

The present invention generally relates to a hand-held fluid discharger and applicator device configured for discharging and applying a fluid, and more specifically relates to a device for discharging and applying a fluid to the skin, or in any surface for household use and so on.

B. Description of Related Art

Generally, as part of a wet shaving process or a skin caring and cosmetic process, a user applies a skin preparation or a fluid to their skin using a brush, or their hands prior to shaving their hair in the skin, or for treating their skin, or for treating any surfaces. The preparation or fluids may be soap, foam, gel, lotion, etc. For hygienic treatment, it is recommended to apply the fluid on the skin using a sponge rather than using their bare fingers. Further, holding the sponges using the bare-fingers for treatment is also unhygienic, as it will restrict the free airflow through the sponge. This action further obstructs effective penetration of fluid through the skin pores. In addition, these sponges get wet and become too hard to hold it through the bare fingers during the application over the skin.

The use of cosmetic wedges in bare hand to enable a person to dip and apply the fluid for treating their skin, or any surfaces is well-known in the art. As further known in the art, the shaving system comprises skin care facilities by using soft sponge like material or a lubricating strip coupled to the shaving cartridge for easy dip and application of shaving lotion, creams, moisturizer and other cosmetic thereof. However, this is a messy and lengthy process, which requires the use of multiple products/tools such as cosmetic wedges bare hand or shaving cartridge to enable a person to dip and apply the fluid for treating their skin, or any surfaces. Even though the present art eliminates the use of sponges, brushes, lubricating strip or the like during shaving process, but they lack in uniform discharge and application of the fluids to the user's skin or on any surfaces.

Therefore, there is a need for a device capable of uniformly discharging, distributing or applying the fluid for treating the skin or any other surfaces. There is also exists a need for a device comprising a handle for introduction and application of the fluid to the skin.

SUMMARY OF THE INVENTION

The present invention relates to a fluid discharger and applicator device for uniform distribution or application of the fluid for treating the skin or any surface. In an embodiment, the fluid discharger and applicator device comprises a handle, a dispenser connector and a dispenser member. In one embodiment, the handle of the fluid discharger and applicator device is defined with a cavity to store one or more fluids. The handle is further defined with a dispenser end configured to dispense the fluid stored within the cavity. In an embodiment, the dispenser connector of the fluid discharger and applicator device is removably fastened to the dispenser end of the handle. In one embodiment, the dispenser connector is configured to transfer the fluid extruded from the cavity of the handle on the dispenser member, which is operably attached to the dispenser connector. The dispenser member of the fluid discharger and applicator device is configured to apply the fluid on skin of a user.

In an embodiment, the handle is a flask, a cartridge, a tube, a box or a plate, which defines the cavity in it. In one embodiment, the fluid discharger and applicator device comprising the handle defined with the cavity is configured to refillable with the fluid. In an embodiment, the handle is openable and closeable type. The handle may be layered, where one layer of the handle is removably fastened to the other layer to enable opening and closing of the layers in the handle. In an embodiment, the handle and the dispenser member is disposable, or reused. The handle is retrofitted via the dispenser end to the dispenser connector integrated with the dispenser member. In one embodiment, the handle comprises at least one of a pliable plastic or a rubber material. In one embodiment, the handle is provided with a circular or an elliptical cross section. In another embodiment, the handle is provided with a grip, a grooved, a rough or an etched glass surface.

In one embodiment, the dispenser connector is removably fastened via a threaded connection, snap-fit connection, or a friction type connection to the dispenser end of the handle. In an embodiment, the dispenser member is imbedded to a base of the dispenser connector. In one embodiment, the dispenser member comprises one of a sponge-like material, a hydrophilic foam pad, a latex-free sponge material or a rubber-like material. In an embodiment, the dispenser member comprises a cone-shaped structure made of soft rubber-like material. In one embodiment, the dispenser connector transfers the fluid through a plurality of holes in the cone-shaped structure to the user skin.

In one embodiment, the fluid comprises at least one of a liquid, a pre-shave lotion, a gel, a moisturizer, a skin cream and a paste. In an embodiment, the fluid discharger and applicator device further comprises a holder to hang the device in up-right position, where the fluid is prevented to further flow due to gravity during a standby mode.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

FIG. 4 shows a schematic view of the fluid discharger and applicator device with a tubular handle in elliptical cross section according to another embodiment.

DETAILED DESCRIPTION OF EMBODIMENTS

A description of embodiments of the present invention will now be given with reference to the Figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that evolve within the meaning and range of equivalency of the claims are to be embraced within their scope.

Figure 1B:
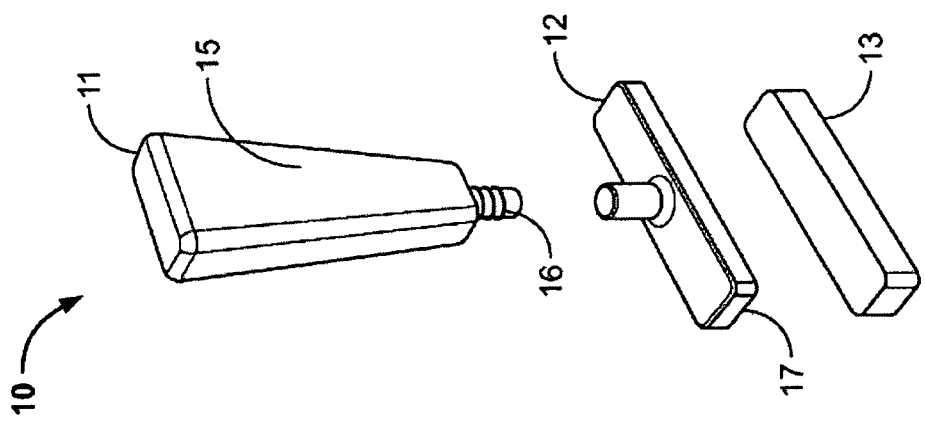
FIG. 1B shows exploded views of the fluid discharger and applicator device with the flask handle.
Figure 1A:
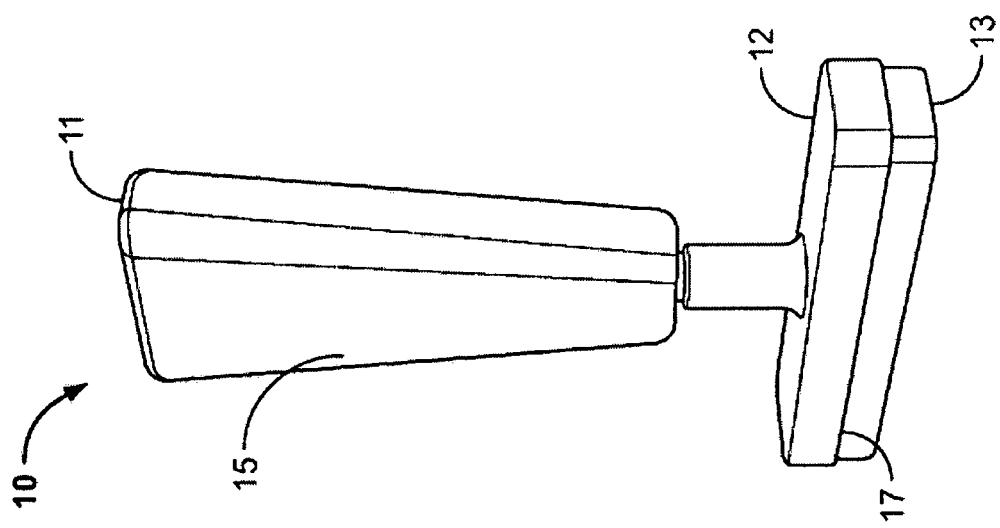
FIG. 1A shows a perspective view of the fluid discharger and applicator device with a flask handle according to an embodiment.

The present invention relates to a fluid discharger and applicator device 10 for uniform discharge, distribution or application of the fluid for treating the skin or any surface. Referring to FIG. 1A and FIG. 1B, the fluid discharger and applicator device 10 comprises a handle 11, a dispenser connector 12 and a dispenser member 13. In one embodiment, the handle 11 of the fluid discharger and applicator device 10 is defined with a cavity 15 to store one or more fluids. The handle 11 is further defined with a dispenser end 16 configured to dispense the fluid stored within the cavity 15. In an embodiment, the dispenser connector 12 of the fluid discharger and applicator device 10 is removably fastened to the dispenser end 16 of the handle 11. In one embodiment, the dispenser connector 12 is configured to transfer the fluid extruded from the cavity 15 of the handle 11 on the dispenser member 13, which is operably attached to the dispenser connector 12. The dispenser member 13 of the fluid discharger and applicator device 10 is configured to apply the fluid on the skin of a user.

In an embodiment, the handle 11 is a flask, a cartridge, a tube, a box or a plate, which defines the cavity 15 in it. In one embodiment, the fluid discharger and applicator device 10 comprising the handle 11 defined with the cavity 15 is refillable with the fluid. In an embodiment, the handle 11 is disposable, or reused. The handle 11 is retrofitted via the dispenser end 16 to the dispenser connector 12 integrated with the dispenser member 13. In one embodiment, the handle 11 comprises at least one of a pliable plastic or a rubber material.

In one embodiment, the dispenser connector 12 is removably fastened via a threaded connection, snap fit connection, or a friction type connection to the dispenser end of the handle 11. In an embodiment, the dispenser member 13 is imbedded to a base 17 of the dispenser connector 12. In one embodiment, the dispenser member 13 comprises one of a sponge-like material, a hydrophilic foam pad, a latex-free sponge material or a rubber-like material. In one embodiment, the fluid comprises at least one of a liquid, a pre-shave lotion, a gel, a moisturizer, a skin cream and a paste. In an embodiment, the dispenser member 13 is disposable, or reused.

Referring to FIG. 1A and FIG. 1B, shows a perspective and exploded view of the fluid discharger and applicator device 10 with flask handle 11 according to an embodiment. The fluid discharger and applicator device 10 comprises flask handle 11 with the cavity 15 and the dispenser end 16, attached to the dispenser connector 11 with the integrated dispenser member 13. In one embodiment, the dispenser end 16 of the flask handle 11 is attached to the dispenser connector 12 by threaded connection. The dispenser end 16 of the flask handle 11 is twisted into the dispenser connector 12.

In an embodiment, the user applies pressure on the flask handle 11 to extrude the required amount of fluids such as pre-shave oil. In one embodiment, the user squeezes the flask handle 11 to extrude the required amount of fluids. In another embodiment, the user application of the pressure or squeeze on the flask handle 11 depends on the viscosity of the oil. In an embodiment, the fluid flows from the cavity 15 of the flask handle 11 through the dispenser connector 12 into the dispenser member 13. The user could apply fluid on the skin by placing the dispenser member 13 on the skin.

Figure 2B:
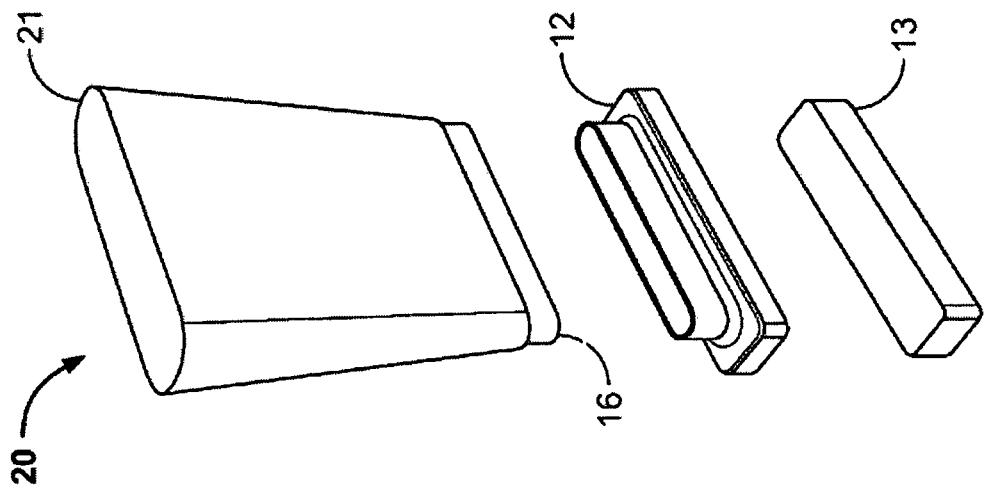
FIG. 2B shows an exploded view of the fluid discharger and applicator device with the cartridge handle.
Figure 2A:
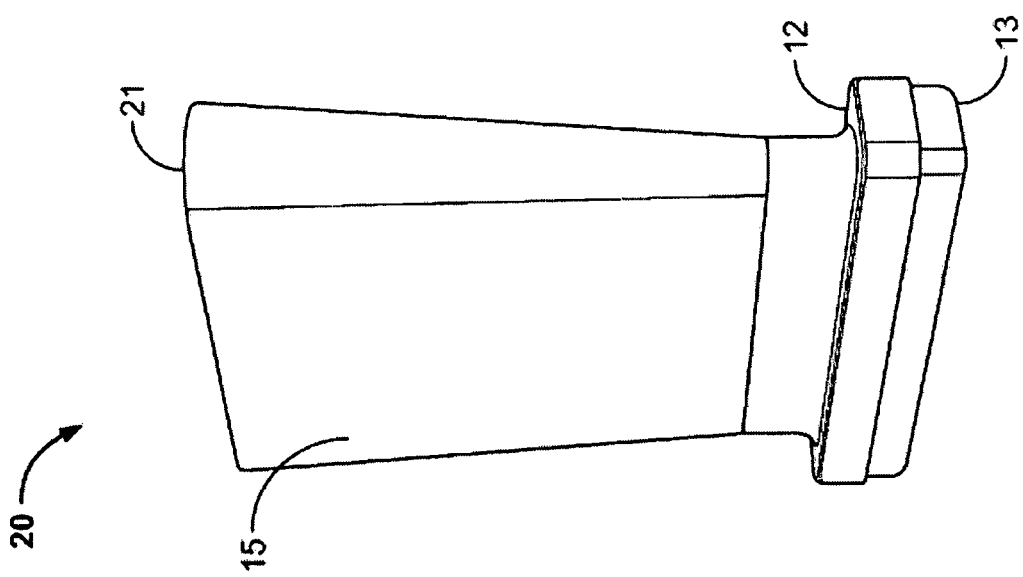
FIG. 2A shows a perspective view of the fluid discharger and applicator device with a cartridge handle according to another embodiment.

Referring to FIG. 2A and FIG. 2B, shows a perspective and exploded view of the fluid discharger and applicator device 20 with a cartridge handle 21 according to an embodiment. The fluid discharger and applicator device 20 comprises cartridge handle 21 with cavity 15 and dispenser end 16, attached to the dispenser connector 12 with the integrated dispenser member 13. In one embodiment, the dispenser end 16 of the cartridge handle 21 is attached to the dispenser connector 12 by snap-fit or friction type connection. The dispenser end 16 of the cartridge handle 21 is right-sized to clamp into the dispenser connector 12.

In an embodiment, the user applies pressure on the cartridge handle 21 to extrude the required amount of fluids such as pre-shave oil. In one embodiment, the user squeezes the cartridge handle 21 to extrude the required amount of fluids. In another embodiment, the user application of the pressure or squeeze on the cartridge handle 21 depends on the viscosity of the oil. In an embodiment, the fluid flows from the cavity 15 of the cartridge handle 21 through the dispenser connector 12 into the dispenser member 13. The user could apply fluid on the skin by placing the dispenser member 13 on the skin.

Figure 3B:
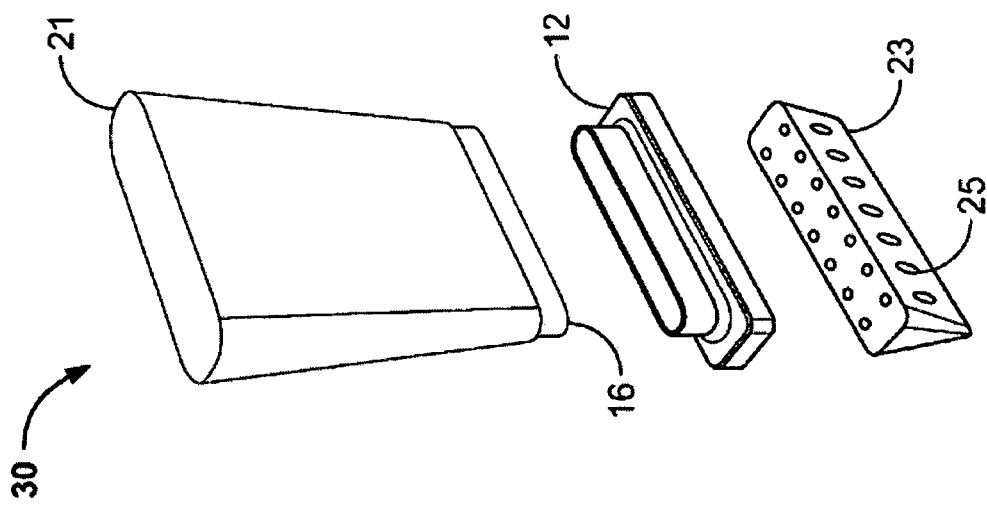
FIG. 3B shows an exploded view of the fluid discharger and applicator device with the cone-shaped dispenser member.
Figure 3A:
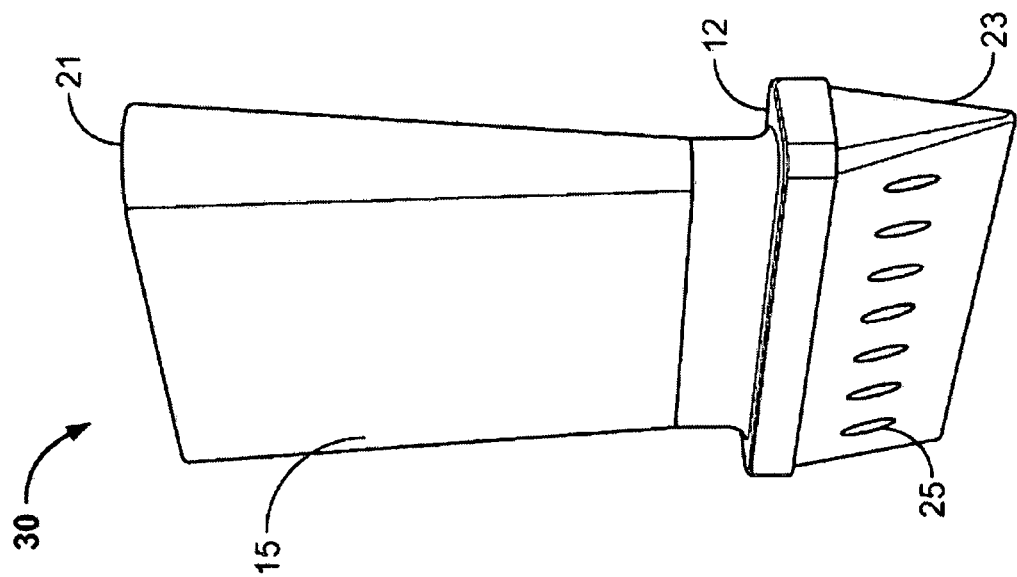
FIG. 3A shows a perspective view of the fluid discharger and applicator device with a cone-shaped dispenser member according to another embodiment.

Referring to FIG. 3A and FIG. 3B, shows a perspective and exploded view of the fluid discharger and applicator device 30 with a with a cone-shaped dispenser member 23 according to an embodiment. In an embodiment, the fluid discharger and applicator device 30 mentioned in FIGS. 3A and 3B is similar to the fluid discharger and applicator device 20 with the cartridge handle 21 referred in FIG. 2A and FIG. 2B, except the dispenser member 23. In an embodiment, the dispenser member 23 is a cone-shaped structure made of soft rubber-like material. In one embodiment, the dispenser member 23 is a spatula structure made of soft rubber-like material. In one embodiment, the fluid flows from the dispenser connector 12 through plurality of holes 25 inside the cone-shaped structure. The soft rubber material is used to bend while applying the fluid against the skin, and disperse the fluid flowing through the holes 25 on the skin.

FIG. 4 shows a schematic view of the fluid discharger and applicator device 40 with tubular handle 31 in elliptical cross section according to another embodiment. In one embodiment, the dispenser member 13 is fixed to the handle 31, where the surface of the handle 31 may have a characteristic angled cut 33 at an end for firm holding by the user. In one embodiment, the dispenser member 13 is a sponge head. The width of the dispenser member 13 ranges from about 20 mm to 40 mm, and the length of the handle 31 ranges from about 90 mm to 100 mm.

Figure 5:
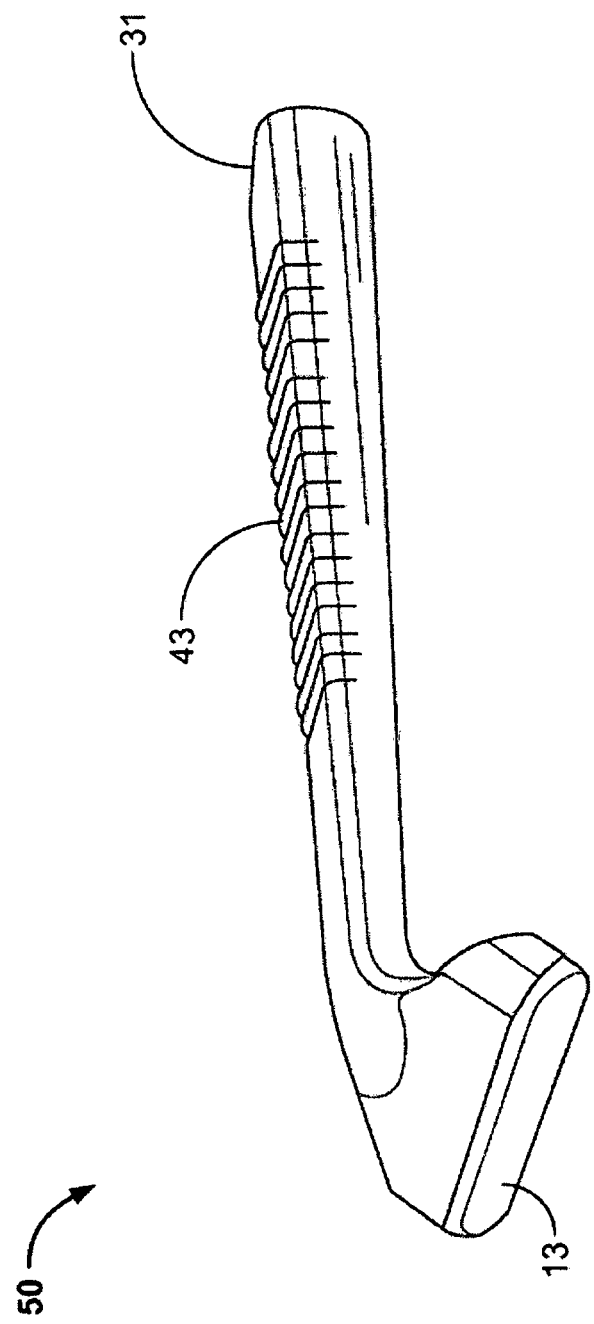
FIG. 5 shows a schematic view of the fluid discharger and applicator device with the tubular handle with a grip structure according to another embodiment.

FIG. 5 shows a schematic view of the fluid discharger and applicator device 50 with the tubular handle 31 with a grip structure 43 according to another embodiment. In one embodiment, the dispenser member 13 is fixed to the handle 31, where the surface of the handle 31 may have a non-smooth surface for firm holding by the user. In another embodiment, the dispenser member is fixed to the handle 31, where the surface of the handle may have a non-smooth bold and solid lined surface for firm holding by the user. In one embodiment, the dispenser member 13 is a sponge head. The width of the dispenser member 13 ranges from about 20 mm to 40 mm, and the length of the handle 31 ranges from about 90 mm to 100 mm.

Figure 6:
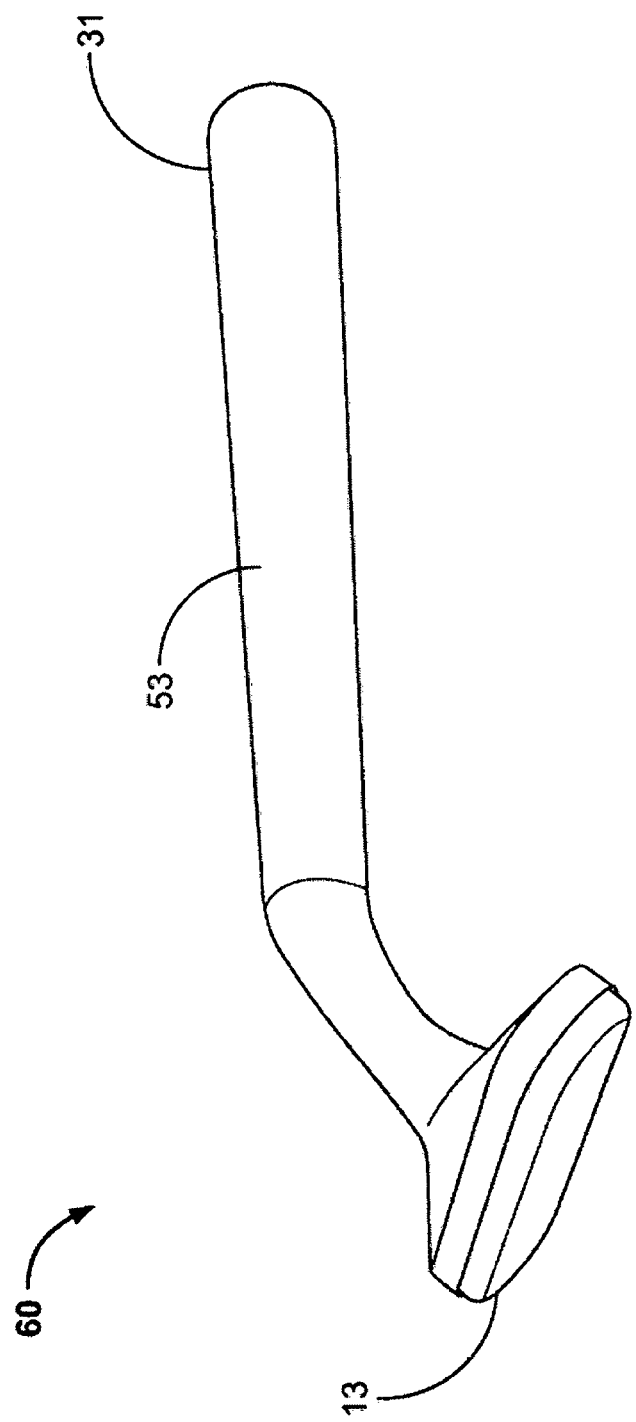
FIG. 6 shows a schematic view of the fluid discharger and applicator device with a tubular handle in circular cross section according to another embodiment.

FIG. 6 shows a schematic view of the fluid discharger and applicator device 60 with a tubular handle 31 in circular cross section 53 according to another embodiment. In one embodiment, the dispenser member 13 is fixed to the handle 31, where the surface of the handle 31 may have a smooth surface for a smooth feel by the user. In one embodiment, the dispenser member 13 is a sponge head. The width of the dispenser member 13 ranges from about 20 mm to 40 mm, and the length of the handle 31 ranges from about 90 mm to 100 mm.

Figure 7:
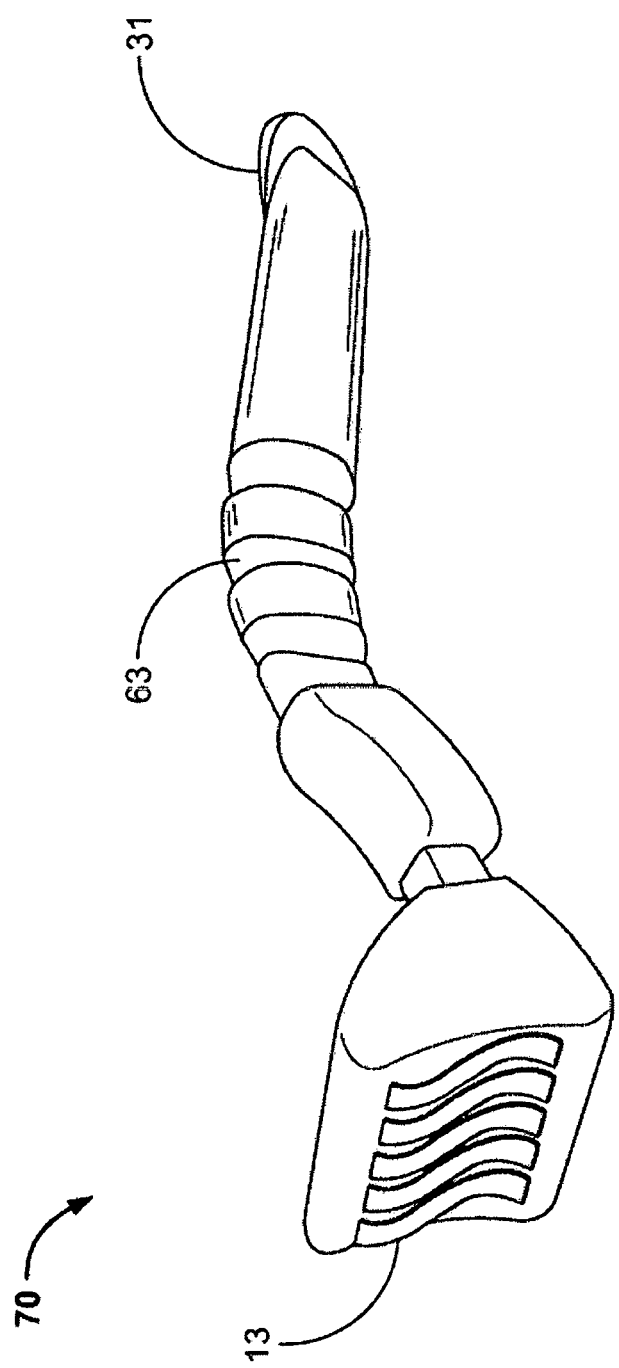
FIG. 7 shows a schematic view of the fluid discharger and applicator device with the tubular handle with a groove structure according to another embodiment.
Figure 8A:
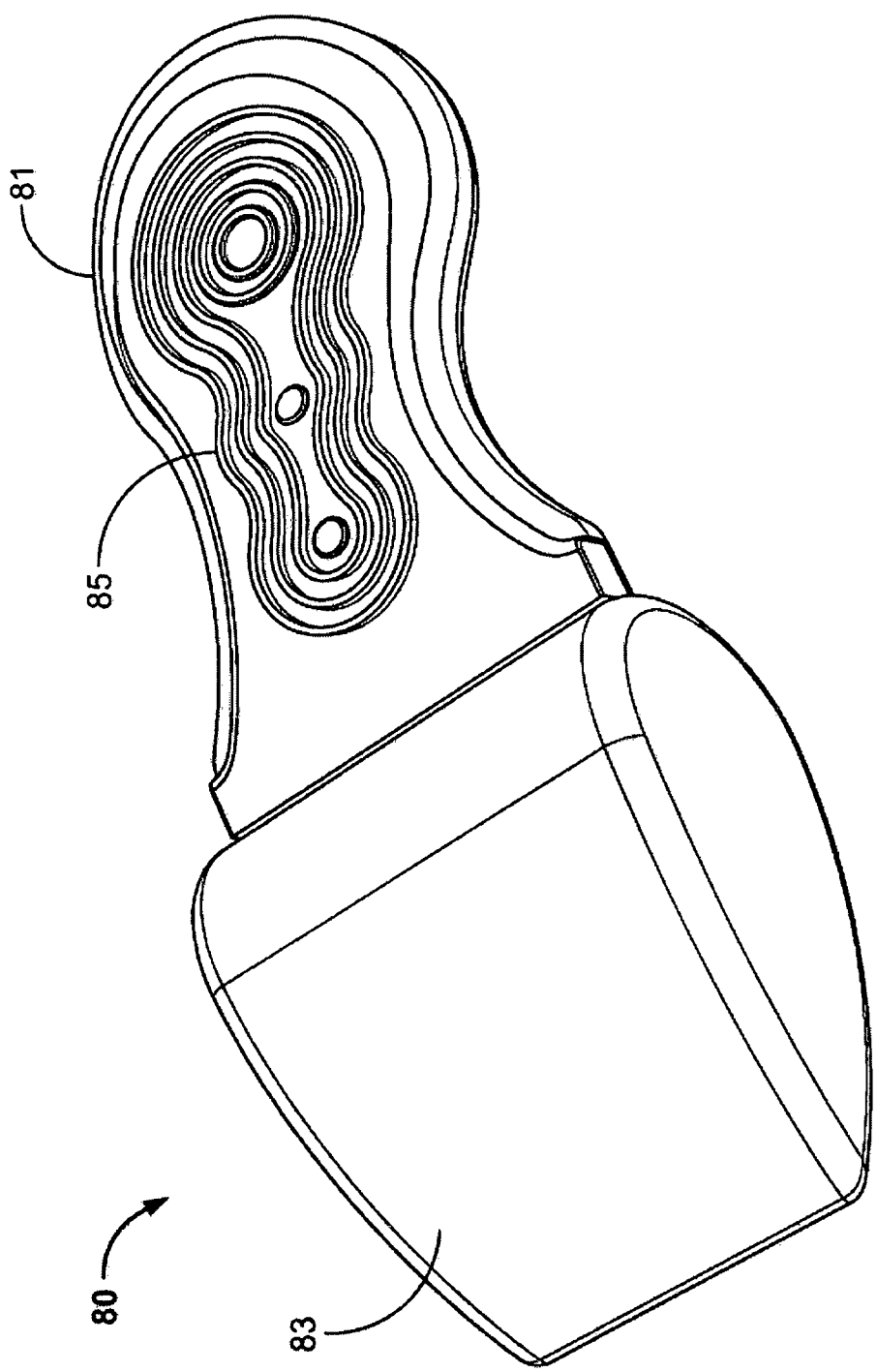
FIG. 8A shows a schematic view of the fluid discharger and applicator device with a flat handle according to another embodiment.
Figure 8B:
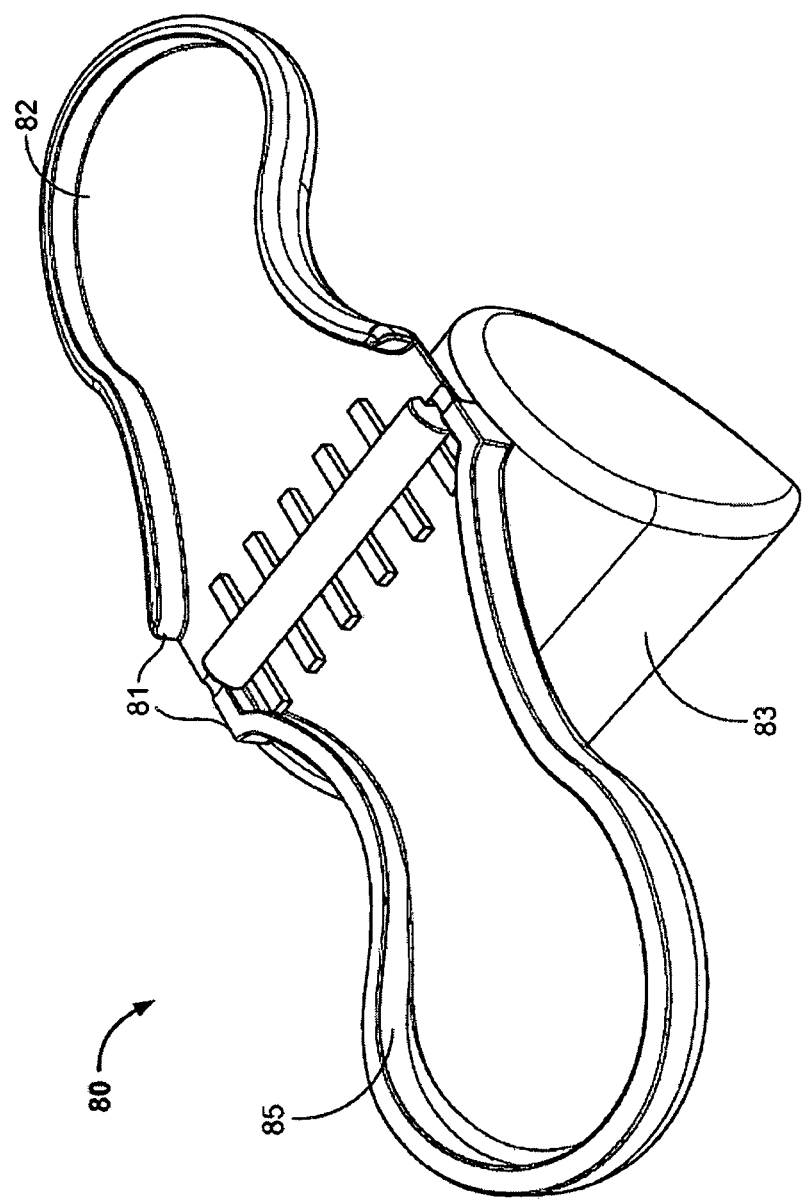
FIG. 8B shows a schematic view of the fluid discharger and applicator device with an openable and closeable type flat handle according to another embodiment.

FIG. 7 shows a schematic view of the fluid discharger and applicator device 70 with the tubular handle 31 with a groove structure 63 according to another embodiment. In one embodiment, the dispenser member 13 is fixed to the handle 31, where the surface of the handle 31 may have a rough or groove surface for firm holding by the user. The width of the dispenser member 13 ranges from about 20 mm to 40 mm, and the length of the handle 31 ranges from about 90 mm to 100 mm. FIG. 8A shows a schematic view of the fluid discharger and applicator device 80 with a flat handle 81 according to another embodiment. In one embodiment, the dispenser member 83 is fixed to the handle, where the surface of the flat handle 81 may have an etched glass designed surface 85 for firm holding by the user. In one embodiment, the dispenser member 83 is a wedge shaped structure. FIG. 8B shows a schematic view of the fluid discharger and applicator device 80 with an open-able and closeable type flat handle 81 according to another embodiment.

In an embodiment, the handle 81 is open-able and closeable type. The handle may be layered, where one layer 82 of the handle is removably fastened to the other layer 85 to enable opening and closing of the layers in the handle 81. In an embodiment, the handle 81 is opened to refill with the fluids and closed while applying the fluid on the user's skin. In one embodiment, the dispenser member 83 is a wedge shaped structure for cosmetic application.

Figure 9:
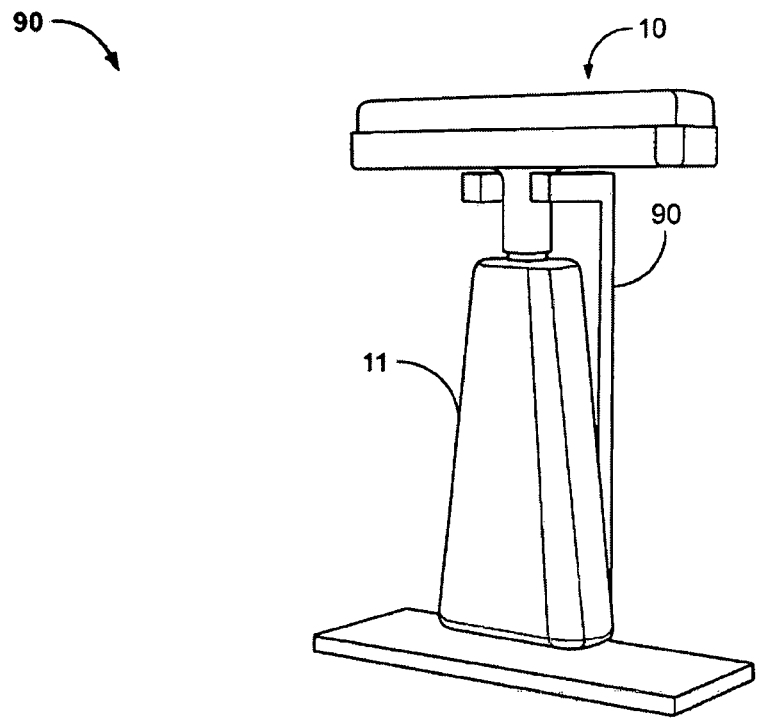
FIG. 9 shows a perspective view of a holder for hanging the fluid discharger and applicator device according to an embodiment.

Referring to FIG. 9 shows a perspective view of a holder 90 for hanging the fluid discharger and applicator device 10 according to an embodiment. In an embodiment, the fluid discharger and applicator device 10 further comprises a holder to hang the device 10 in up-right position. The holder 90 is designed to prevent the flow of fluid due to gravity during a standby mode. FIG. 9 shows a perspective view of a holder 90 for hanging the fluid discharger and applicator device 10 with the flask handle 11 for an example. The design of the holder 90 could be customized in accordance to the other designs of the handle according to an embodiment.

Figure 10:
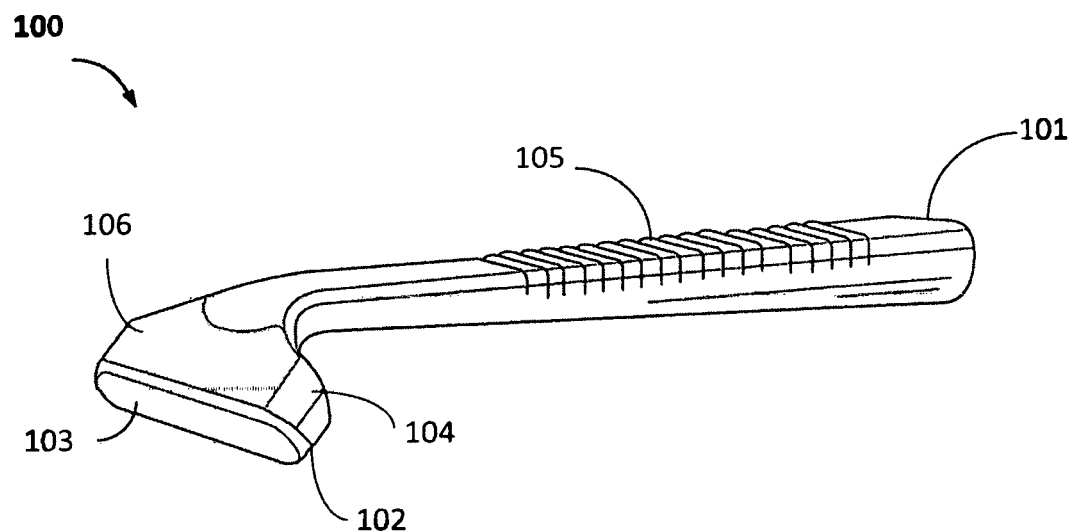
FIG. 10 shows a perspective view of a fluid discharger and applicator device with a pressing part made of flexible materials according to another embodiment.

FIG. 10 shows an embodiment of a fluid discharger and applicator device 100. The fluid discharger and applicator device 100 includes a handle 105 and an applicator 102 connected to the handle 105. The applicator 102 includes an application head holding member 104 and an application head 103. The application head holding member 104 is provided with a pressing part 106. The pressing part 106 may be pressed into the applicator head holding member 104, squeezing the applicator head 103, and thereby pressing out the fluid in the applicator head 103.

In this embodiment, the application head holding member 104 is a housing including an open end. The end 101 of the housing opposite to the open end is connected to one end of the handle 105. The housing includes an internal configuration adapted to the application head, so that the application head 103 can be at least partially retained in the housing, for example by being embedded in the housing. The application side is exposed a proper length from the open end for contacting, the user's skin, for example, so as to apply the fluid to be applied to the skin.

In this embodiment, the pressing part 106 can be pressed, thereby squeezing out the fluid in the application head. In this embodiment, the pressing part 106 is made of flexible materials. The flexible materials may include a rubber material, for example. In this embodiment, the pressing part 106 is provided on the surrounding wall between the open end of the housing and the opposite end 101 opposite to the open end. The housing may be made of a rigid material, and the rigid material may be, for example, a hard plastic or metal material.

In such embodiment, the pressing part 106 may be provided on a part of the application head holding member 104 opposite to the application side, and the pressing part 106 may be connected with the other part of the application head holding member 104 by any technique known to those skilled in the art. For example, it can be over-molded onto the application head holding member 104 for holding the applicator head 103. When in use, a certain force can be applied by pressing or squeezing the pressing part 106 to apply the fluid to be applied to the skin of the user, for example.

In this embodiment, there is an elastically fixed connection between the handle 105 and the applicator 102, so that the fluid discharger and applicator device can be slightly bent during use to increase the comfort feeling of user. The handle 105 and applicator 102 can be integrally formed. The angle between the applicator 102 and the handle 105 along the longitudinal axis is between about 60 degrees and about 80 degrees, so that the application fluid or the 'fluid' or the 'pre-shave oil' can be applied to, for example, the skin of the user in an easy and comfortable manner.

Figure 11:
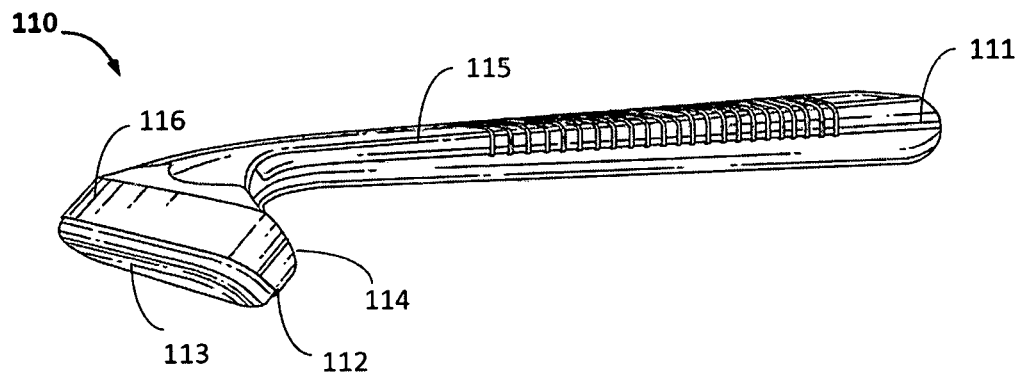
FIG. 11 shows a perspective view of a fluid discharger and applicator device with a pressing part made of flexible materials according to another embodiment.

FIG. 11 shows a perspective view of a fluid discharger and applicator device with a pressing part made of flexible materials according to another embodiment.

In this embodiment, the fluid discharger and applicator device 110 includes a handle 115 and an applicator 112 connected to the handle 115. The applicator 112 includes an application head holding member 114 and an application head 113. The application head holding member 114 is provided with a pressing part 116. The pressing part 116 may be pressed so as to squeeze the applicator head 113, and thereby pressing out the fluid in the applicator head 113. The pressing part 116 is made of flexible materials as in the embodiment in FIG. 10. The pressing part 116 is provided along the whole sounding wall of the application head holding member 114. For example, the pressing part 116 made of rubber material is wrapped around application head holding member 114.

Figure 12A:
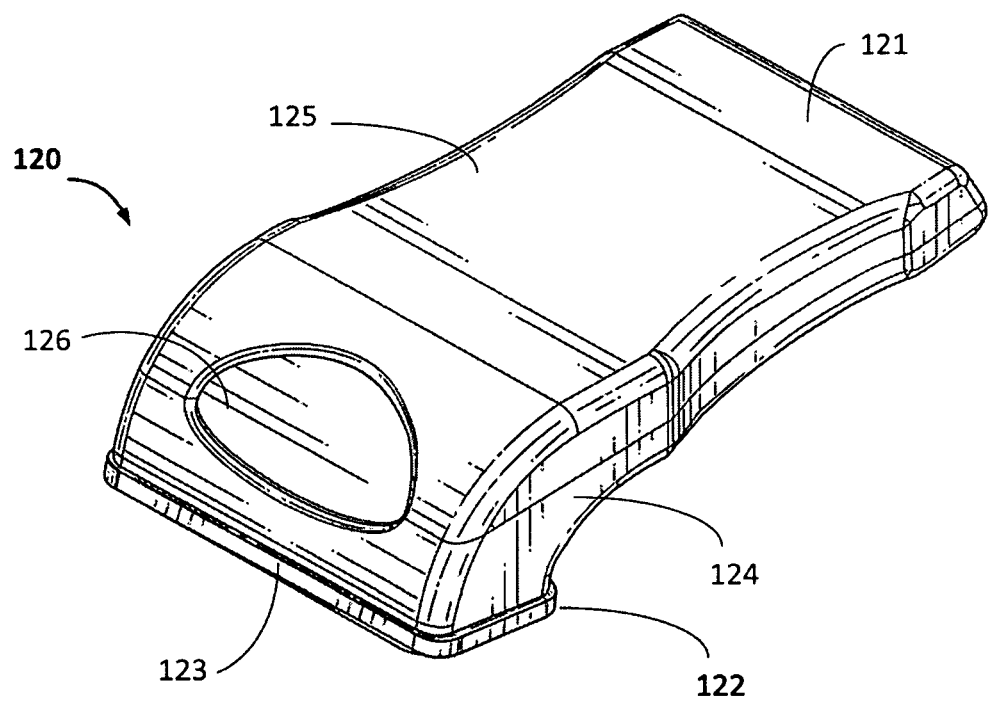
FIG. 12A shows a perspective view of a fluid discharger and applicator device with a pressing part comprising a notch and a pressing piece extending out from the notch according to another embodiment.
Figure 12B:
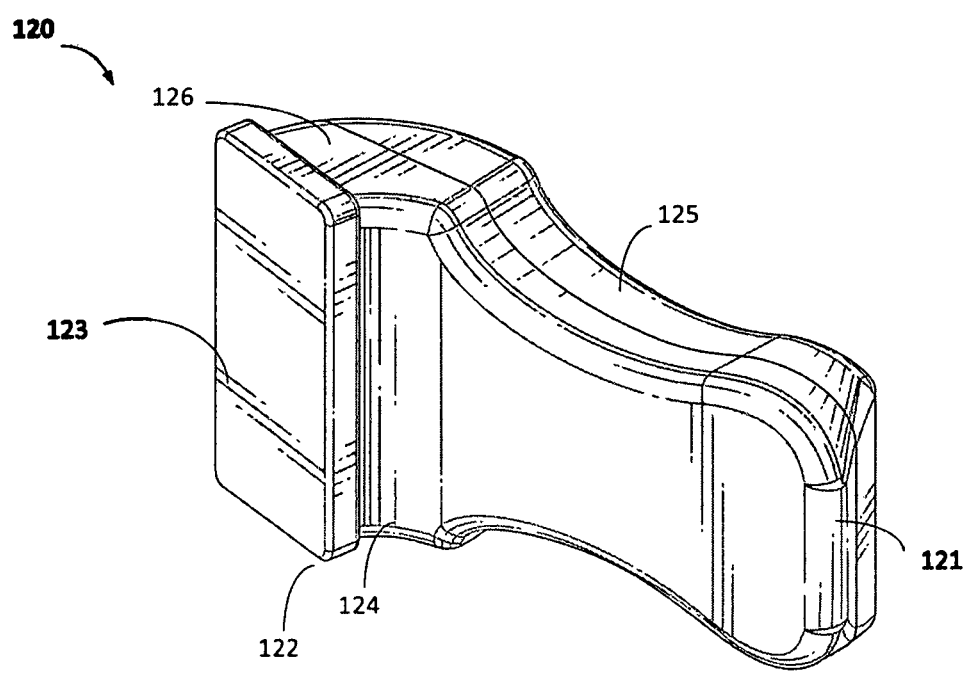
FIG. 12B shows another perspective view of the fluid discharger and applicator in FIG. 12A.

FIG. 12A shows a perspective view of a fluid discharger and applicator device with a pressing part comprising a notch and a pressing piece extending out from the notch according to another embodiment. FIG. 12B shows another perspective view of the fluid discharger and applicator in FIG. 12A.

In this embodiment, the fluid discharger and applicator device 120 includes a handle 125 and an applicator 122 connected to the handle 125. The applicator 122 includes an application head holding member 124 and an application head 123. The application head holding member 124 is provided with a pressing part 126 comprising a notch and a pressing piece.

In this embodiment, the pressing part 126 and the housing is made of the same material, and the pressing piece includes a protrusion extending from the notch, so that the user can easily and accurately identify the position of the pressing piece, and make the pressing piece be pressed into the housing to squeeze the applicator head to apply the fluid to be applied to, for example, the skin of the user.

Figure 13A:
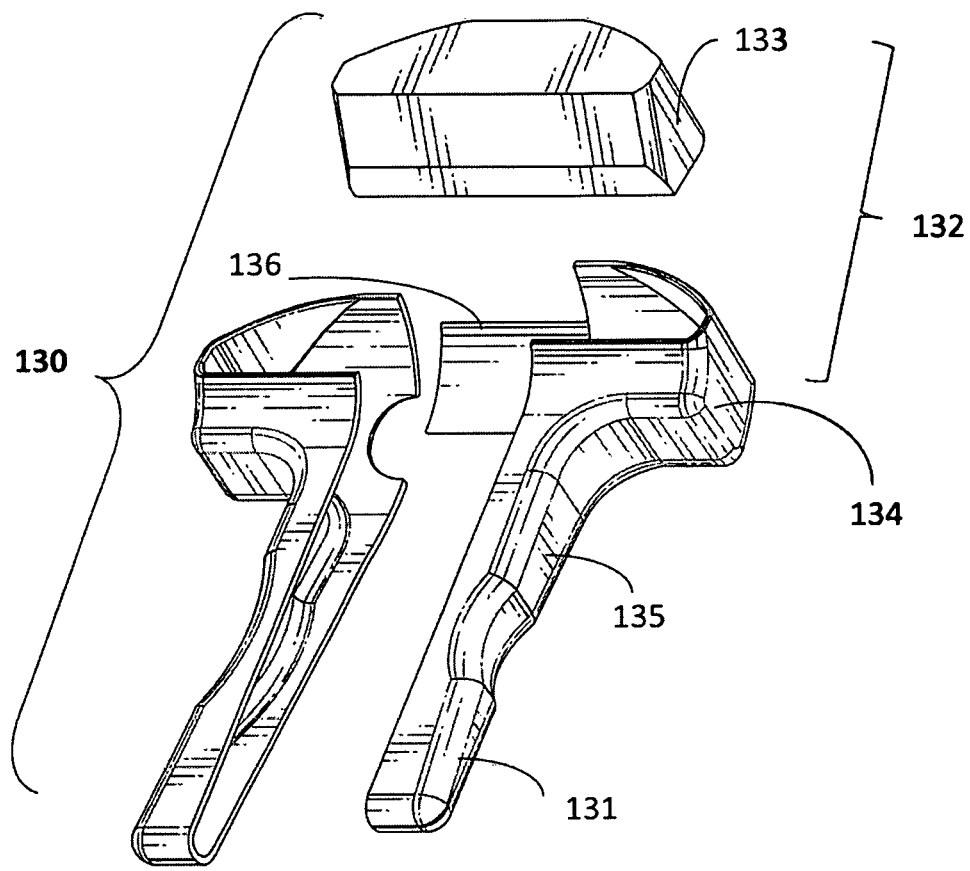
FIG. 13A shows an exploded perspective view of a fluid discharger and applicator device with a pressing part comprising a notch and a pressing piece according to another embodiment.
Figure 13B:
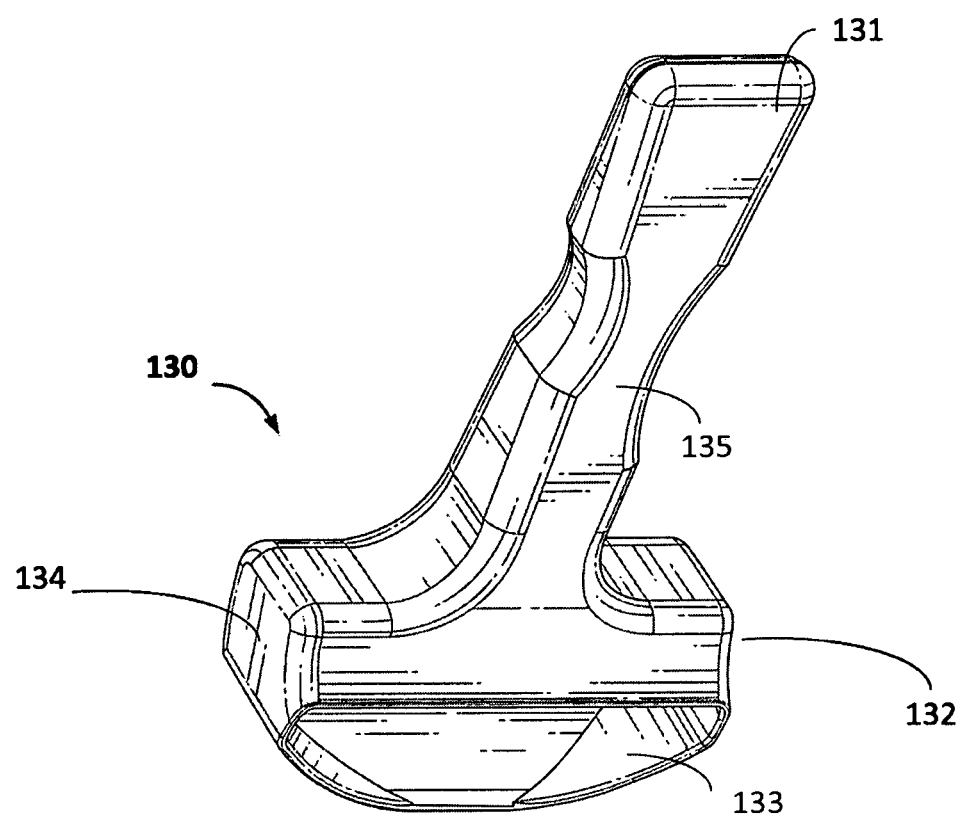
FIG. 13B shows a perspective view of the fluid discharger and applicator device of FIG. 13A.

FIG. 13A shows an exploded view of an embodiment of a fluid discharger and applicator device 130, which more clearly shows the structure of the fluid discharger and applicator device 130 with a pressing part 136. FIG. 13B shows an perspective view of the fluid discharger and applicator device of FIG. 13A.

In this embodiment, the fluid discharger and applicator device 130 includes a handle 135 and an applicator 132. The applicator 132 includes an application head holding member 134 and an application head 133. A pressing part 136 is provided on the application head holding member 134. The pressing part 136 may be pressed into the applicator head holding member 134, thereby pressing the applicator head 133 to press out the fluid in the applicator head 133.

In this embodiment, a notch is provided on the portion of the application head holding member 134 opposite to the application side. The pressing part 136 is a planar pressing piece that matches the shape of the notch but has a slightly larger size. The planar pressing piece and the notch are correspondingly arranged between the side of the application head 133 opposite to the application side and the application head holding member 134, and the pressing piece is exposed from the notch so that the pressing part 136 can be pressed from the notch to squeeze the application head 133. Therefore, during use, a certain force can be applied to press or squeeze the pressing part 136 to apply the fluid to be applied to, for example, the skin of the user.

Figure 14A:
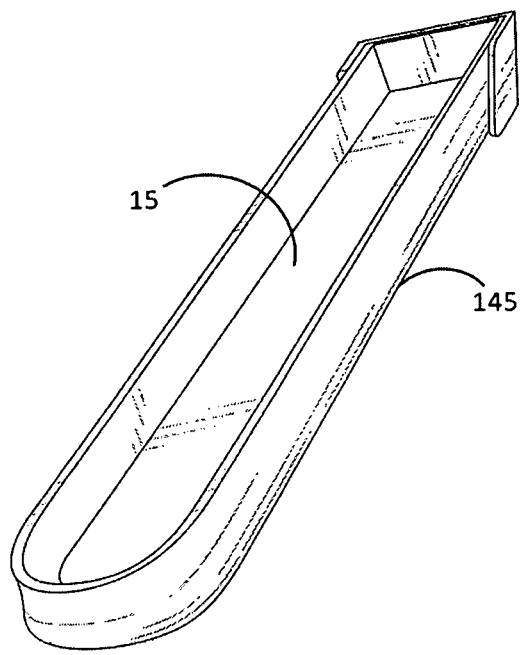
FIG. 14A-14B shows a rectangular shaped elongated handle of the fluid discharger and applicator device, according to an embodiment.
Figure 14B:
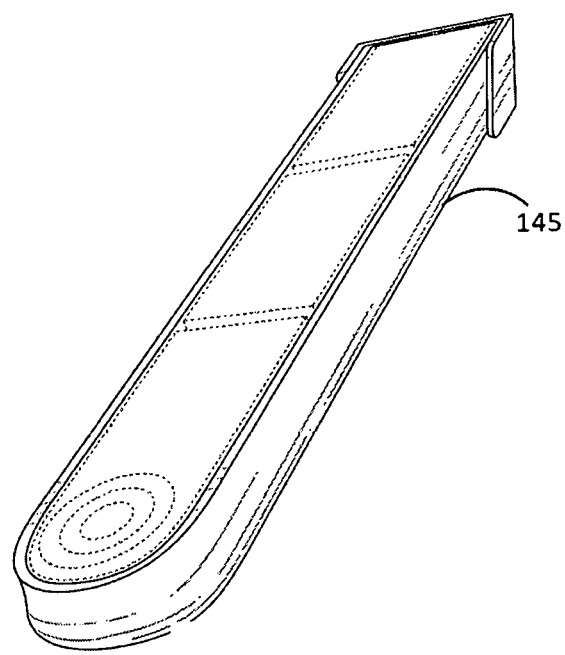
Figure 14C:
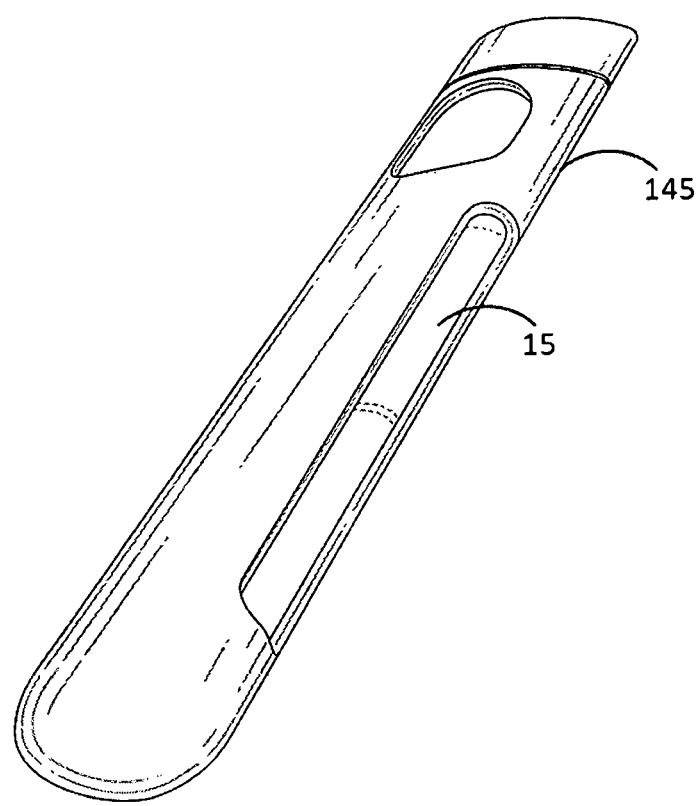
FIG. 14C shows an elliptical shaped elongated handle of the fluid discharger and applicator device, according to an embodiment.
Figure 14D:
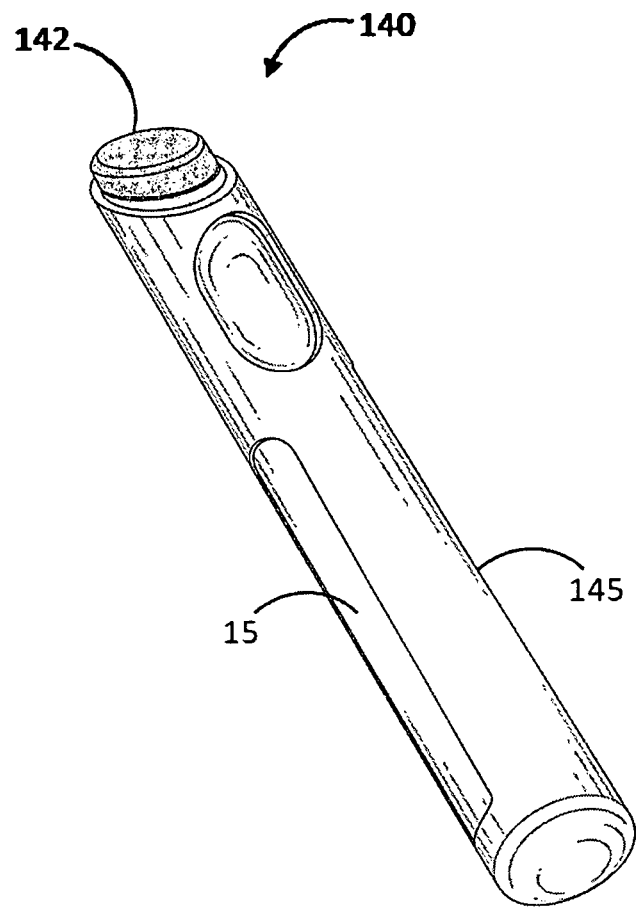
FIG. 14D shows the fluid discharger and applicator device with the elliptical shaped elongated handle shown in FIGS. 14C, according to an embodiment.
Figure 14E:
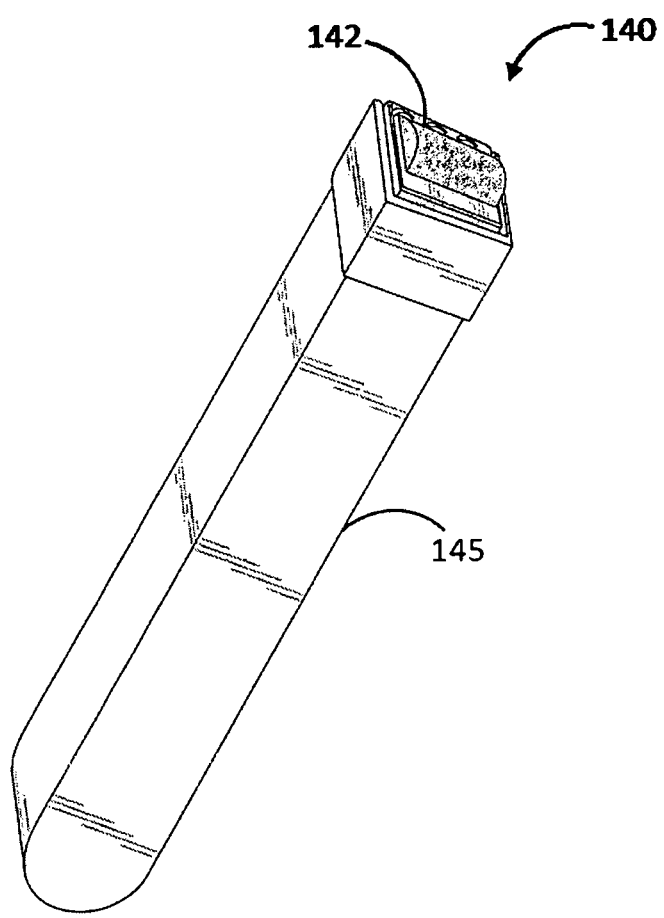
FIG. 14E shows the fluid discharger and applicator device with the rectangular shaped elongated handle shown in FIGS. 14A-14B, according to an embodiment.

FIG. 14A-14B shows a rectangular shaped elongated handle 145 of the fluid discharger and applicator device, according to an embodiment of the present invention. In one embodiment, as shown in FIG. 14A, the rectangular shaped elongated handle 145 has a square or rectangular shaped cross section with an elongated cavity 15 within the handle 145. In one instance, the cavity 15 is used to store the fluid such as the pre-shave oil for dispensing through the applicator. FIG. 14B shows the handle 145 with the cavity 15 being sealed with a closing member on top of the cavity 15. In one instance, the closing member for sealing the top of the cavity 15 is detachable to fill the cavity 15 with the fluid or for cleaning purpose. In some other instances, the fluid is filled in the cavity 15 through an opening on a top or bottom portion or anywhere on the handle 145. In a yet another instance, the cavity 15 is divided into one or more compartments for storing the fluid. FIG. 14C shows the elliptical shaped elongated handle 145 of the fluid discharger and applicator device. The elliptical shaped elongated handle 145 has an elliptical shaped cross section according to an alternate embodiment of the present invention. The handle 145 with the elliptical shaped cross section includes the cavity 15, which is accessible through an opening on the handle 145. In one instance, at least a portion of the handle 145 is transparent to allow the user to view a level of fluid left within the cavity 15. Accordingly, various types of cross sections, such as circular, zigzag, etc., for the handle 145 can be formed to store desired amount of the fluid and to provide good, desired appearance to the fluid discharger and applicator device. FIG. 14D shows the fluid discharger and applicator device with the applicator 142 attached to the elliptical shaped elongated handle 145 shown in FIG. 14C, according to an embodiment. The pre-shave oil or the fluid is stored within the cavity 15 of the elliptical shaped elongated handle 145 and is dispensed using the applicator 142. FIG. 14E shows the fluid discharger and applicator device 140 with the applicator 142 attached to the rectangular shaped elongated handle 145 shown in FIGS. 14A-14B, according to an embodiment. The pre-shave oil or the fluid is stored within the cavity 15 of the rectangular shaped elongated handle 145 and is dispensed using the applicator 142. In one instance, the elliptical or rectangular shaped elongated handle 145 is provided with a button which is configured to be operable by a user by applying pressure to dispense the fluid from the cavity 15. In a yet another instance, the cavity 15 within the elliptical or rectangular shaped elongated handle 145 can be filled with one or more readily available fluid cassettes to dispense the fluid through the applicator.

Figure 15F:
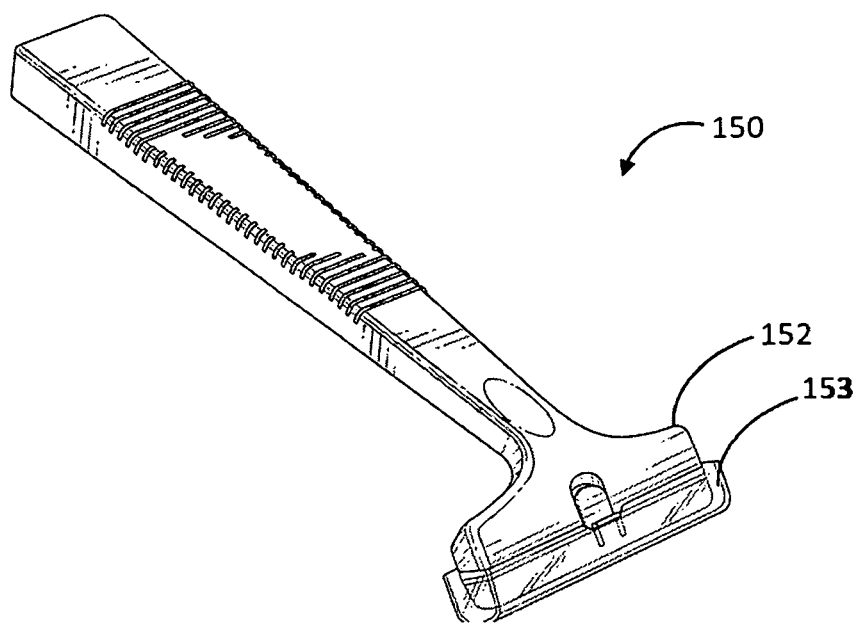
FIG. 15F-15G shows the fluid discharger and applicator device with its applicator covered using a detachable lid, according to an embodiment.
Figure 15G:
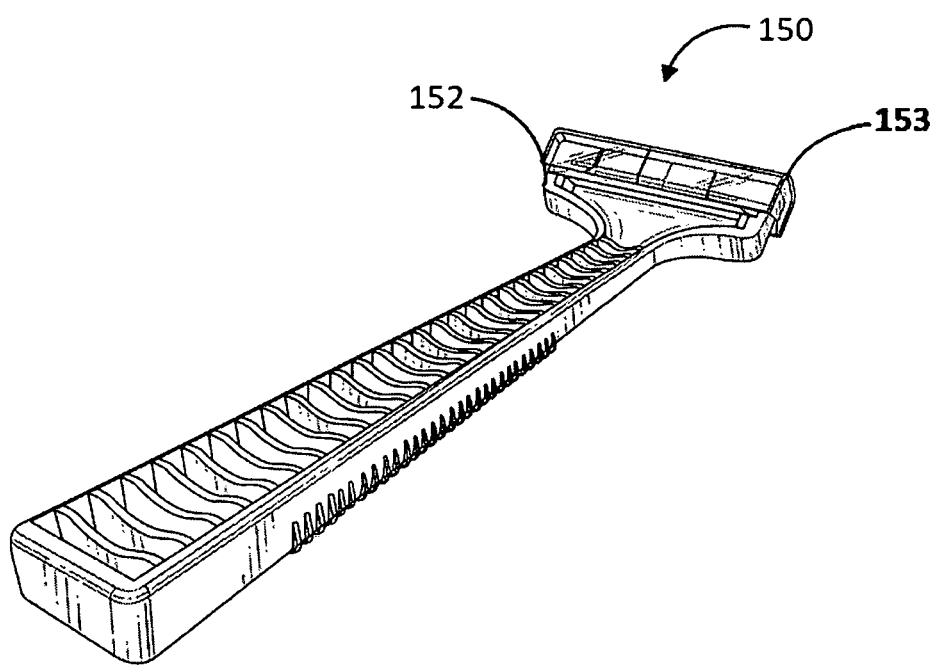
Figure 16A:
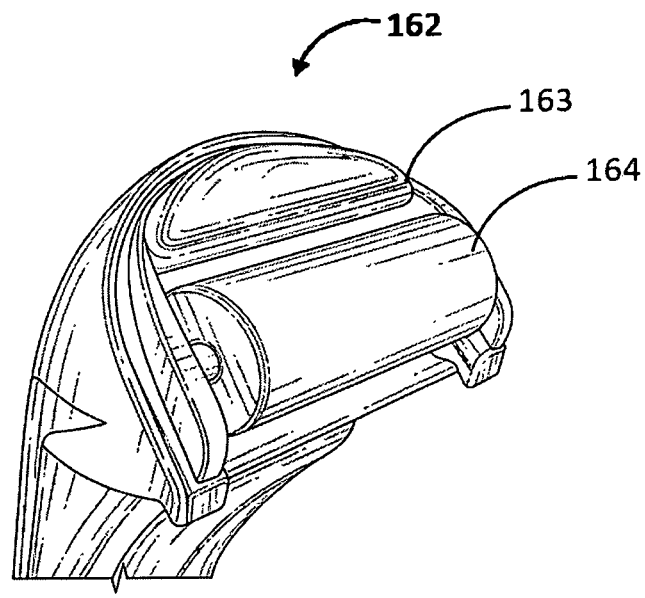
FIG. 16A shows the fluid discharger and applicator device with a roller attached to the applicator, according to an embodiment.
Figure 16B:
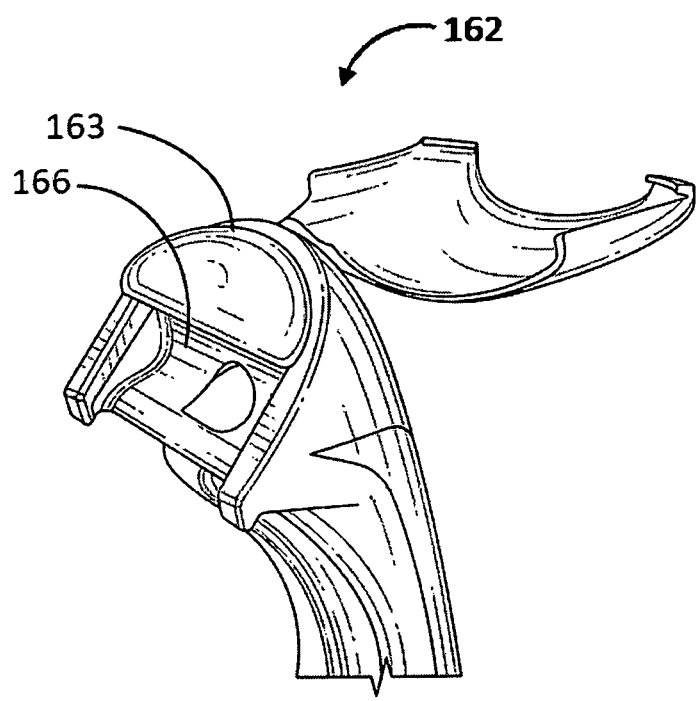
FIG. 16B shows a groove of the fluid discharger and applicator device configured to receive the roller shown in FIG. 16A, according to the embodiment.
Figure 16C:
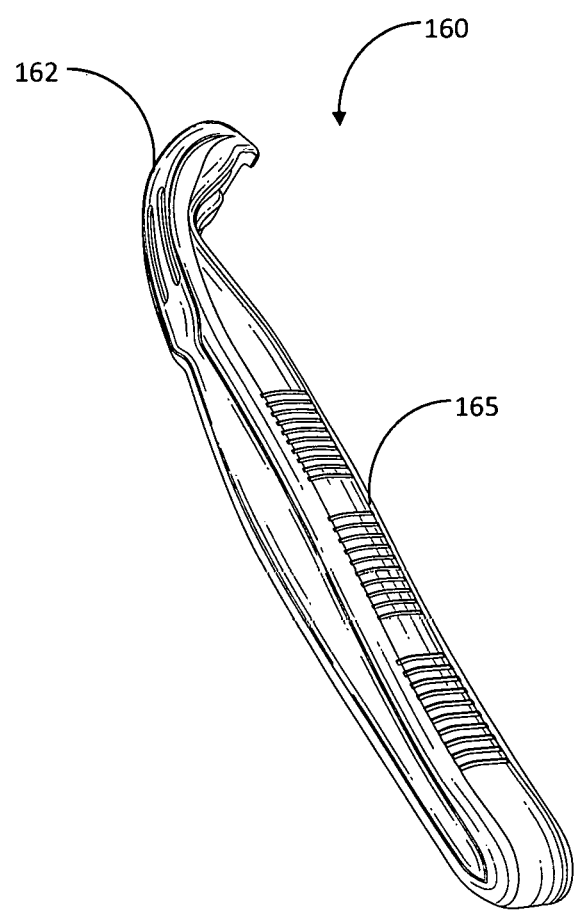
FIG. 16C-16D shows first and second side perspective views of the fluid discharger and applicator device configured to operably receive the roller onto the applicator, according to an embodiment.
Figure 16D:
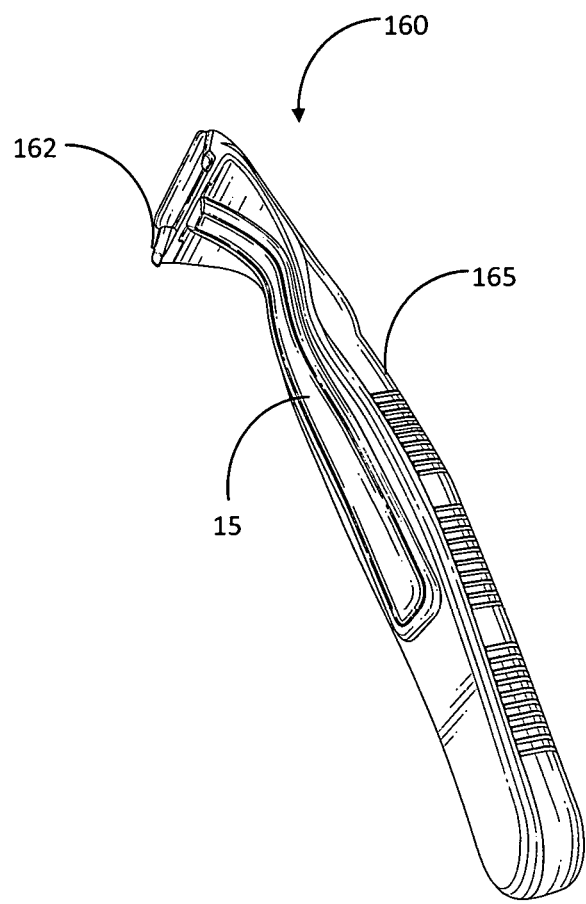
Figure 16E:
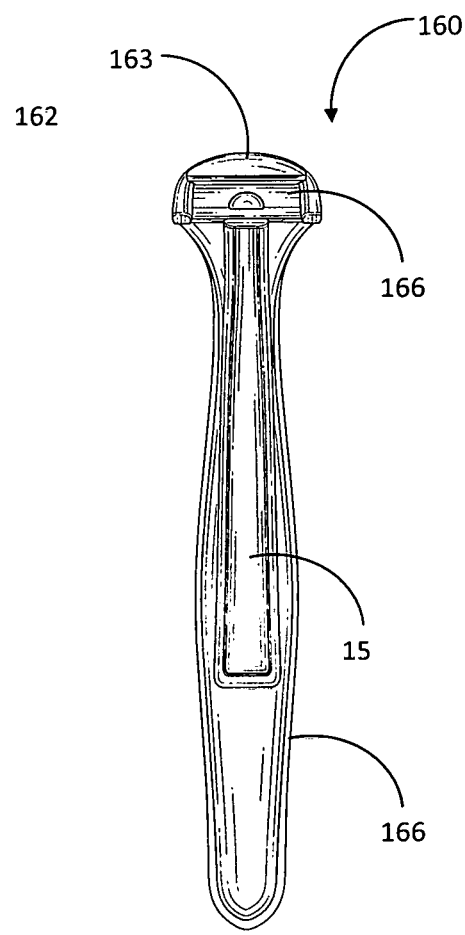
FIG. 16E shows a front view of the fluid discharger and applicator device shown in FIG. 16C-16D, according to the embodiment.
Figure 16F:
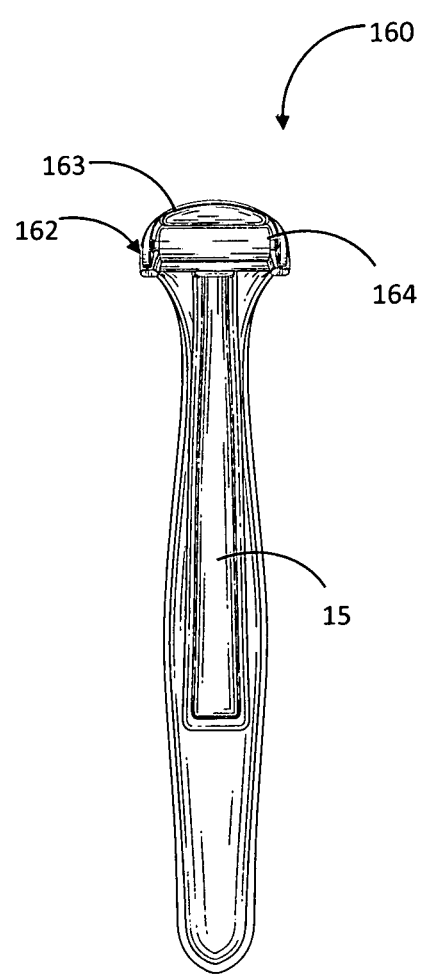
FIG. 16F shows a front view of the fluid discharger and applicator device shown in FIG. 16E with the roller attached to the applicator, according to an embodiment.
Figure 16G:
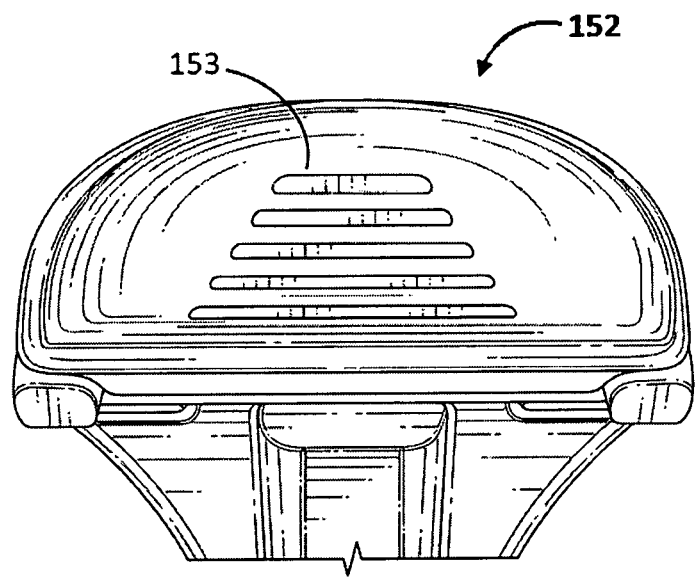
FIG. 16G shows the fluid discharger and applicator device with its applicator covered using a lid, according to an embodiment.
Figure 16H:
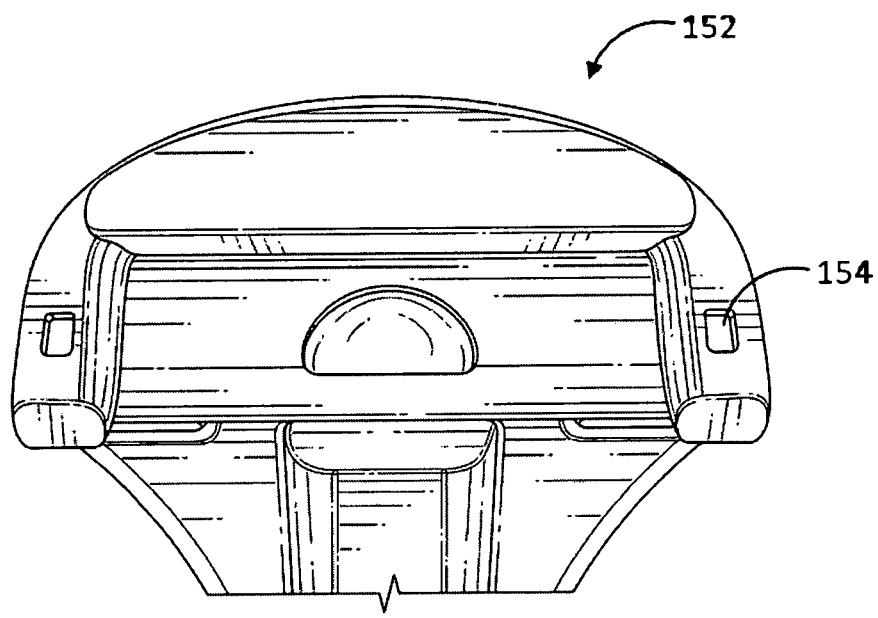
FIG. 16H shows the applicator of the fluid discharger and applicator device with a pair of grooves configured to detachably receive the lid, according to the embodiment.
Figure 16I:
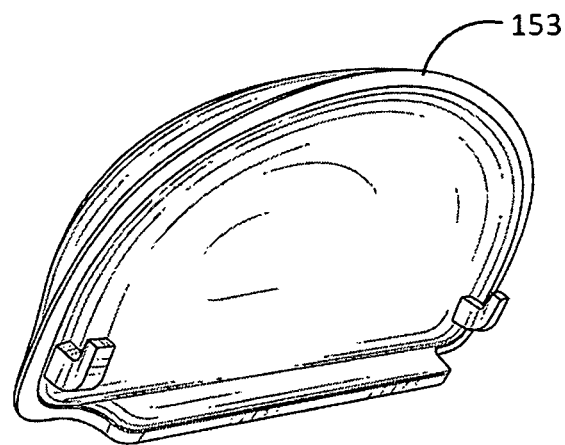
FIG. 16I shows the lid configured to engage with the pair of grooves on the applicator shown in FIG. 16H, according to the embodiment.
Figure 16J:
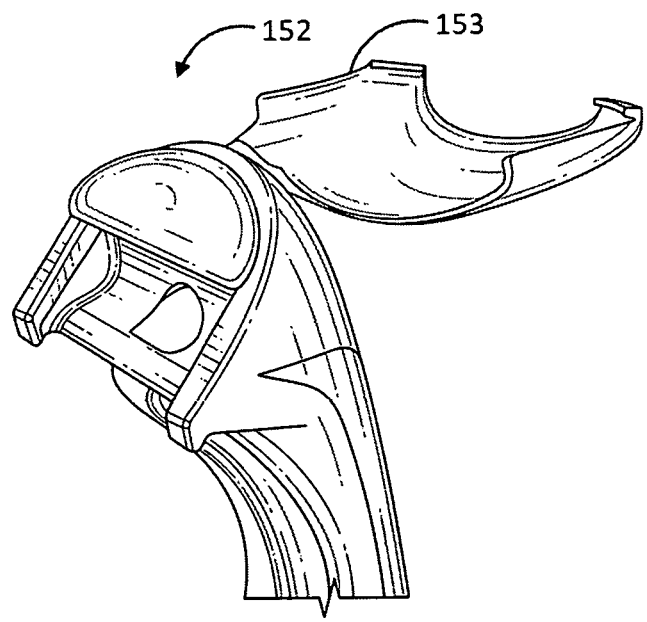
FIG. 16J shows a lid hinged to a top portion of the applicator and kept in an open position prior to use of the fluid discharger and applicator device, according to an embodiment.
Figure 16K:
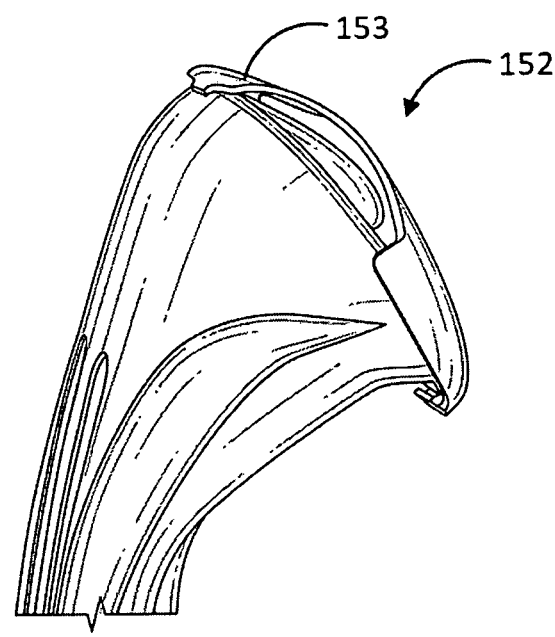
FIG. 16K shows the lid shown in FIG. 16J in a closed position covering the applicator, according to the embodiment.

FIG. 16G shows the fluid discharger and applicator device with its applicator 152 covered using a lid 153, according to an embodiment of the present invention. In one instance, the lid 153 is detachably connected to the applicator 152. The applicator 152 is provided with a pair of slots 154 as shown in FIG. 16H. The lid 153 includes a pair of projections or engaging means as shown in FIG. 16I to detachably engage with the corresponding pair of slots 154 provided on the applicator 152, thereby appropriately covering the applicator 152. In a yet another instance, the applicator 152 is provided with a hinge on its top surface, the hinge is configured to receive the lid 153. The lid 153 can be opened about the hinge as shown in FIG. 16J prior to use of the fluid discharger and applicator device and can be closed to cover the applicator 152 after use of the fluid discharger and applicator device, as shown in FIG. 16K. FIG. 15F-15G shows the fluid discharger and applicator device 150 with its applicator 152 covered using a detachable lid 153, according to an alternate embodiment of the present invention. The user can remove the lid 153 by pulling the lid 153 out of engagement from the applicator 152 prior to use of the fluid discharger and applicator device 150. Further the user can cover the applicator 152 by placing the lid 153 over the applicator and pushing it to secure over the applicator 152. In one instance, both the lid 153 and the applicator 152 are provided with complementary engaging mechanisms to secure the lid 153 over the applicator 152.

In one embodiment, the applicator 162 of the fluid discharger and applicator device is provided with a roller 164 as shown in FIG. 16A. In one instance, the roller 164 is rotatably attached to the applicator 162 below the application head 163. In one embodiment, at least a portion of the roller 164 is positioned in a recessed groove 166 on the applicator 162, as shown in FIG. 16B. In one instance, the roller 164 is rotatably fixed within the recessed groove 166 on the applicator 162. In another instance, the roller 164 rotatably fixed within the recessed groove 166 on the applicator 162 is detachable. The roller 164 assists in application of a uniform layer of the fluid such as the pre-shave gel onto the skin of the user using the application head 163.

FIG. 16C-16E shows a first and second side perspective views and a front view of the fluid discharger and applicator device 160, according to an embodiment. The applicator 162 of the fluid discharger and applicator device 160 is configured to operably receive the roller 164 within the recessed groove 166 below the application head 163. In one instance, the handle 165 of the fluid discharger and applicator device 160 includes the cavity along the length of the handle 165. The cavity within the handle 165 stores the pre-shave oil or gel or the fluid or the application fluid cassette and is dispensed through the opening on top of the handle 165 into the applicator 162. In one instance, the handle 165 includes one or more openings which can be manually opened and closed to allow filling of the pre-shave oil or gel or the fluid. In one instance, the shell of the application head holding member is provided with a hole communicating with the fluid stored in the handle 165 in an end opposite to an open end exposed to the user. The channel provided within the handle 165 connects the cavity and the hole of the shell of the application head holding member, and the fluid or the fluid cassette is arranged so that the fluid is allowed to be pressed out and penetrated into the application head only when a pressure is applied at a corresponding portion of the handle 165.

In one embodiment, the handle 165 includes a button which when pressed by the user pushes the fluid from the cavity to the applicator 162 through the opening on top of the handle 165. In a yet another embodiment, the user can press anywhere on the surface of the handle 165, exterior to the cavity, to release the fluid from the cavity to the applicator 162 through the opening on top of the handle 165. In one instance, the handle 165 with the cavity is permanently attached or fabricated to the applicator 162. This allows easy transfer of the fluid from the cavity of the handle 165 to the applicator 162 through a continuous tubing or channel connecting the handle 165 and the applicator 162. In a yet another instance, the handle 165 with the cavity is detachably connected to the applicator 162. In such instances, both the handle 165 and the applicator 162 include holes, which get connected to form the continuous tubing or channel connecting the handle 165 and the applicator 162 when assembled. In one instance, a check valve is provided in the channel to control the flow of the fluid. The check valve gets opened when the user presses on the corresponding portion or the button of the handle 165 to dispense the fluid into the shell of the application head holding member. In certain instances, the exterior of the cavity, i.e. at the surface of the handle 165, is transparent to enable the user to view a current level of the fluid stored in the handle 165.

FIG. 16F shows a front view of the fluid discharger and applicator device 160 shown in FIG. 16E with the roller 164 attached to the applicator 162, according to an embodiment. In certain instances, the applicator 162 is provided with the recessed groove 166 below the applicator head 163 to rotatably receive the roller 164. The roller 164 assists in application of a uniform layer of the fluid such as the pre-shave gel onto the skin of the user using the application head 163. In an alternate embodiment, the roller 164 rotatably attached to the applicator 162 is fed with the fluid through one or a pair of ends of the roller 164 operably engaged to the applicator 162. The roller 164 is provided with a plurality of holes to dispense the fluid. This further helps in the application of a uniform layer of the fluid such as the pre-shave gel onto the skin of the user. In some instances, the roller 164 is attached with material similar to the applicator head 163, i.e. capable of storing the fluid, for application of a uniform layer of the fluid such as the pre-shave gel onto the skin of the user.

In one embodiment, the handle and the applicator can be connected by a detachable connection, such as a threaded connection or a snap-fit connection. In one embodiment, the handle may define a cavity therein, and the cavity is used to store the application fluid or the application fluid replacement device. The housing of the application head holding member is provided with an orifice in fluid communication with the cavity of the handle in the end opposite to the open end, and is used for conveying the fluid to be applied to the application head. In one embodiment, the handle may be provided with a channel connecting the cavity and the orifice of the housing of the applicator head holding member. The application fluid or application fluid replacement device is arranged such that only when a certain pressure is applied at the corresponding part on the handle, the application fluid can be pressed out, through the orifice or channel, and penetrated into the application head, readying for application to the skin. In one embodiment, a check valve or one-way valve may also be provided in the channel to prevent the fluid immersed in the applicator head from flowing back into the cavity of the handle.

In one embodiment, the applicator head may be filled with application fluid in advance, and no application fluid is stored in the handle. In one embodiment, the fluid discharger and applicator device is a disposable device.

The advantage of the fluid discharger and applicator device is capable of uniformly distributing or applying the fluid for treating the user's skin, or any surface. The device further efficiently utilizes the amount of fluid such as liquid, pre-shave lotion, gel, moisturizer, skin cream or paste to the user's skin. The device allows the low-viscosity fluids, which is applied for daily use in a convenient and hygienic way. The fluid discharger and applicator device assist for providing longevity, rejuvenating and younger looking skin. Further, the device could be used for any type of skin-based applications such as anti-aging skin care, etc.

The foregoing descriptions comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Although specific terms may be employed herein, they are used only in generic and descriptive sense and not for purposes of limitation. Accordingly, the present invention is not limited to the specific embodiments illustrated herein.

What is claimed is:

1. A fluid discharger and applicator device, comprising: a handle, and
an applicator connected to one end of the handle, comprising:
an application head which is able to absorb a fluid and contact a skin of a user and apply the fluid on the skin of the user; and
an application head holding member for holding the application head,
wherein the application head comprises an application side and a pressing part arranged on the application head holding member,
wherein the pressing part is able to press and squeeze the application head so that the fluid inside the application head is pressed out.

2. The fluid discharger and applicator device according to claim 1, wherein the application head is flexible.

3. The fluid discharger and applicator device according to claim 1, wherein the pressing part is made up of flexible materials.

4. The fluid discharger and applicator device according to claim 1,
wherein the pressing part comprises a pressure plate, which is arranged between an opposite side of the application side of the application head and the application head holding member.

5. A fluid discharger and applicator device, comprising: a handle, and
an applicator connected to one end of the handle, comprising:
an application head which is able to absorb a fluid; and
an application head holding member for holding the application head,
wherein the application head comprises an application side and a pressing part arranged on the application head holding member,
wherein the pressing part is able to press the application head so that the fluid inside is pressed out,
wherein the application head holding member is a shell including an open end, the application head is partially arranged in the shell, the pressing part is arranged on a surrounding wall between a pair of ends of the shell, and the shell is made up of rigid material.

6. The fluid discharger and applicator device according to claim 4, wherein the pressing part and the application head holding member are made of same material, and the pressure plate further includes a protrusion, wherein the pressing part is allowed to be pressed into the application head holding member to squeeze the application head.

7. The fluid discharger and applicator device according to claim 1, wherein the applicator is detachably connected with the handle.

8. The fluid discharger and applicator device according to claim 1, wherein the applicator is flexibly fixed to the handle, so that the fluid discharger and applicator device is able to be slightly bent during use.

9. The fluid discharger and applicator device according to claim 8, wherein an angle between an application surface of the application head and a longitudinal axis of the handle is between 60 and 80 degrees.

10. The fluid discharger and applicator device according to claim 1, wherein the application head is filled with the fluid and the applicator is detachable for disposing after use.

11. The fluid discharger and applicator device according to claim 1, wherein the applicator further includes a roller rotatably attached thereto.

12. The fluid discharger and applicator device according to claim 11, wherein the roller is rotatably attached to the applicator below the application head.

13. The fluid discharger and applicator device according to claim 11, wherein the roller is detachable.

14. The fluid discharger and applicator device according to claim 11, wherein at least a portion of the roller is positioned in a recessed groove on the applicator to assist in application of a uniform layer of the fluid using the application head.

15. The fluid discharger and applicator device according to claim 1, wherein the applicator is provided with a hinge on a top surface to attach a lid.

16. The fluid discharger and applicator device according to claim 15, wherein the lid detachably covers the applicator.

17. The fluid discharger and applicator device according to claim 1, wherein pressing the pressing part squeezes the application head so that the fluid inside the applicator head is pressed out of the application head.

18. A fluid discharger and applicator device, comprising:
    a handle, and
    an applicator connected to one end of the handle, comprising:
        an application head which is able to absorb a fluid, wherein the fluid is in the application head; and
        an application head holding member for holding the application head,
        wherein the application head comprises an application side, wherein the application side is configured to contact a skin of a user and apply the fluid in the application head on the skin of the user,
        a pressing part, wherein the pressing part is arranged on the application head holding member,
        wherein pressing the pressing part squeezes the application head so that the fluid inside the application head is pressed out of the application head.

19. The fluid discharger and applicator device according to claim 18, wherein pressing of the pressing part into the application head holding member squeezes the application head so that the fluid inside the application head is pressed out of the application head.

20. The fluid discharger and applicator device according to claim 18, wherein the fluid comprises one of or any combination of a lotion, a gel, a moisturizer, a skin cream, oil and a paste.

* * * * *